US009777334B2

(12) United States Patent
Tiedge et al.

(10) Patent No.: US 9,777,334 B2
(45) Date of Patent: Oct. 3, 2017

(54) CANCER BLOOD TEST USING BC200 RNA ISOLATED FROM PERIPHERAL BLOOD FOR DIAGNOSIS AND TREATMENT OF INVASIVE BREAST CANCER

(71) Applicant: The Research Foundation for SUNY, Albany, NY (US)

(72) Inventors: Henri Tiedge, New York, NY (US); Anna Iacoangeli, Brooklyn, NY (US); Gerald A. Soff, New Rochelle, NY (US)

(73) Assignee: The Research Foundation for State University of New York, Albany, NY (US)

( * ) Notice: Subject to any disclaimer, the term of this patent is extended or adjusted under 35 U.S.C. 154(b) by 0 days.

(21) Appl. No.: 14/398,092

(22) PCT Filed: Mar. 14, 2013

(86) PCT No.: PCT/US2013/031728
§ 371 (c)(1),
(2) Date: Oct. 30, 2014

(87) PCT Pub. No.: WO2013/165598
PCT Pub. Date: Nov. 7, 2013

(65) Prior Publication Data
US 2015/0087538 A1    Mar. 26, 2015

Related U.S. Application Data

(60) Provisional application No. 61/640,684, filed on Apr. 30, 2012.

(51) Int. Cl.
*C12Q 1/68*    (2006.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 5,670,318 | A | 9/1997 | Tiedge et al. |
| 2005/0164189 | A1* | 7/2005 | Tiedge ............. C12Q 1/6886 435/6.14 |
| 2009/0123928 | A1 | 5/2009 | Wood |
| 2009/0190129 | A1 | 7/2009 | Yguerabide et al. |
| 2011/0039732 | A1 | 2/2011 | Raymond et al. |

FOREIGN PATENT DOCUMENTS

| WO | 2009/132928 A2 | 11/2009 |
|---|---|---|
| WO | 2012/001178 A1 | 1/2012 |

OTHER PUBLICATIONS

Huang et al. Anal. Chem., 1996, vol. 68 pp. 2259-2263.*
Gebauer et al., Drug Discovery Today, 2004, vol. 9, pp. 915-917.*
Applied Biosystems, Isolation of Total RNA from Whole Blood and from Cells Isolated from Whole Blood, 2004, 50 pages.*
Apostolaki et al., Breast Cancer Res. Treat., 2009, vol. 117 pp. 525-534.*
Merrie et al., British Journal of Cancer, 1999, vol. 80(12) pp. 2019-2024.*
MACS, Isolation of mononuclear cells from human peripheral blood by density gradient centrifugation, 2008, 2 pages.*
Wang et al., Dendritic BC I RNA: functional role in regulation of translation initiation, J. Neurosci., 2002, 10232-10241, 22.
Wang et al., Dendritic BCI RNA in translational control mechanisms, J Cell Biol, 2005, 811-21, 171.
Lin et al., Translational control by a small RNA: dendritic BCI RNA targets the eukaryotic initiation factor 4A helicase mechanism, Mol Cell Biol, 2008, 3008-19, 28.
Chen et al., Expression of neural BC200 RNA in human tumours, J. Pathol., 1997, 345-351, 183.
Iacoangeli et al., BC200 RNA in invasive and preinvasive breast cancer, Carcinogenesis, 2004, 2125-2133, 25.
Kolling et al., Efficacy of MRI and mammography for breast-cancer screening in women with a familial or genetic predisposition, N Engl J Med, 2004, 427-37, 351.
Tiedge et al., Primary structure, neural-specific expression, and dendritic location of human BC200 RNA, J. Neurosci., 1993, 2382-2390, 13.
Iqbal et al., IRE1-beta inhibits chylomicron production by selectively degrading MTP mRNA, Cell Metab, 2008, 445-55, 7.
Bieche et al., Molecular profiling of inflammatory breast cancer: identification of a poor-prognosis gene expression signature, Clin Cancer Res, 2004, 6789-95, 10.
Patel et al., Clearance of circulating tumor cells after excision of primary colorectal cancer, Ann. Surg., 2002, 226-31, 235.
McShane et al., Reporting recommendations for tumor marker prognostic studies (REMARK), J Natl Cancer Inst, 2005, 1180-4, 97.
Garnick et al., Combating prostate cancer, Sci. Am., 1998, 75-83, 279.
Taplin et al., Mammography facility characteristics associated with interpretive accuracy of screening mammography, J Natl Cancer Inst, 2008, 876-87, 100.
Miglioretti et al., Radiologist Characteristics Associated With Interpretive Performance of Diagnostic Mammography, JNatl Cancer Inst., 2007, 1854-1863, 99(24).
Piao, Hai-long et al., "Non-Coding RNAs as Regulators of Mammary Development and Breast Cancer", J. Mammary Gland Biol. Neoplasia, 17: 33-42 (2012).

(Continued)

*Primary Examiner* — Mindy G Brown
(74) *Attorney, Agent, or Firm* — Kathleen D. Rigaut; Dann, Dorman, Herrell and Skillman (57) ABSTRACT

Compositions and methods for diagnosing an increased risk for the development of aggressive, invasive breast cancer are provided.

5 Claims, 5 Drawing Sheets

(56) References Cited

OTHER PUBLICATIONS

Noerholm et al., "RNA expression patterns in serum microvesicles from patients with glioblastoma multiforme and controls", BMC Cancer, 12: 22 (2012).

Perez, Damon S. et al., "Long, abundantly expressed non-coding transcripts are altered in cancer", Human Molecula Genetics, 17(5): 642-655 (2008).

International Search Report/Written Opinion, dated Jul. 1, 2013, issued in corresponding International Application No. PCT/US2013/031728, filed Mar. 14, 2013.

Extended European Search Report, issued Dec. 7, 2015, in corresponding European Application No. 13785184.6.

* cited by examiner

CANCER BLOOD TEST USING BC200 RNA ISOLATED FROM PERIPHERAL BLOOD FOR DIAGNOSIS AND TREATMENT OF INVASIVE BREAST CANCER

The present application is §371 application of PCT/US2013/031728 filed Mar. 14, 2013 which claims priority to U.S. Provisional Application No. 61/640,684 filed 30 Apr. 2012, the entire disclosure of each being incorporated by reference herein.

Pursuant to 35 U.S.C. §202(c) it is acknowledged that the U.S. Government has rights in the invention described, which was made with funds from the National Institutes of Health, Grant Number NS046769.

FIELD OF THE INVENTION

The invention is useful for cancer screening, staging, monitoring for chemotherapy treatment responses, cancer recurrence or the like. More specifically, the present invention provides reagents, methods and test kits which facilitate analysis and enumeration of BC200 containing tumor cells isolated from peripheral blood.

BACKGROUND OF THE INVENTION

Several publications and patent documents are cited throughout the specification in order to describe the state of the art to which this invention pertains. Each of these citations is incorporated herein by reference as though set forth in full.

Regulatory RNAs play important roles in the control of gene expression in eukaryotic cells [1; 2]. Regulatory BC RNAs are translational repressors that have been implicated in the regulation of protein synthesis in mammalian nerve cells [3; 4; 5]. BCRNAs are small RNAs (150-200 nt, i.e. distinct from miRNAs) that function by interacting with components of the eukaryotic translational machinery [3; 4; 5]. Specifically, primate BC200 RNA and rodent BC1 RNA target the helicase activity of eukaryotic initiation factor 4A (eIF4A), an abundant canonical translation factor that is required for efficient initiation of mRNAs by unwinding higher-order structure content in their 5' untranslated regions (UTRs) [5]. BC RNAs are not typically expressed in somatic mammalian cell types other than neurons. However, in a notable exception to this neuronal expression specificity, BC200 RNA was found expressed at high levels in human invasive breast carcinoma cells [6; 7]. In contrast, BC200 RNA was not detected in normal human breast epithelial cells or in benign tumors of the breast. The combined data suggested that regulatory BC200 RNA is recruited by invasive or pre-invasive breast carcinoma cells, thus promoting deregulation of cellular translational control [7].

Breast cancer remains a leading cause of death from malignancies in women, despite the fact that a combination of factors, including early detection (e.g. mammography) and improved therapeutic intervention (resection, adjuvant therapy), has in recent years resulted in a decrease of breast cancer mortality in the US [8]. But mammograms suffer from variable and significant false negative rates [9; 10; 11], and therapeutic intervention has been hampered by the lack of indicators, molecular and otherwise, that would aide physicians and patients in breast cancer treatment decisions. In particular, any improvement in our ability to predict treatment outcome, and to prognosticate tumor progression and recurrences, would have immediate clinical utility.

SUMMARY OF THE INVENTION

In accordance with the present invention a diagnostic method for detecting an increased risk of invasive breast cancer in a patient is provided. In one embodiment, an exemplary method entails obtaining a whole blood sample from said patient and isolating and/or measuring the levels of BC200 RNA present in said sample relative to predetermined levels observed in patients selected from the group consisting of i) control patients without evidence of disease; ii) patients having primary disease; iii) patients having metastatic disease. The levels in the patient being tested are compared with those previously determined in i, ii, or iii, wherein patients having levels of circulating BC200 RNA levels which are elevated relative to those observed in i) have an increased risk for the development of aggressive breast cancer.

In an alternative embodiment, the method optionally entails isolation of a peripheral blood mononuclear cell fraction prior to isolation and measuring of said BC200 RNA levels.

The level of BC3200 RNA can be determined using any method known to the skilled artisan, including without limitation, real time PCR, RLS and PWG.

In yet another aspect of the invention, a kit for practicing the methods described herein is provided.

BRIEF DESCRIPTION OF THE DRAWINGS

FIG. 1. BC200 blood levels correlate with patient tumor burden. (A) High levels of BC200 RNA are detected in peripheral blood from a breast cancer patient with metastatic disease. Total RNA was isolated from whole blood. The RT-PCR product was resolved on a 1.2% agarose gel (bands at the bottom of the gel represent primers used in the PCR reaction). Medical history: This patient was diagnosed with breast cancer two years prior to BC200 RNA analysis. She underwent surgery and adjuvant therapy, including 6 cycles of doxorubicin and cyclophosphamide followed by anastrozole (Arimidex). Two years later, she was diagnosed with bone metastases and was scheduled to undergo a new treatment cycle with paclitaxel (Taxol) and trastuzumab (Herceptin). Blood for BC200 analysis was drawn after diagnosis of recurrent disease but before Taxol/Herceptin treatment. It appears that in this case, i.e. prior to the initiation of adjuvant therapy, BC200 blood levels are higher than average BC200 blood levels in metastatic disease. (B) The bar diagram shows qRT-PCR analysis of BC200 expression levels in whole blood from three patient groups and from healthy subjects. BC200 RNA amplification data were normalized to ARP mRNA [13; 14]. Data are shown in the format mean±SEM, with each data point representing three experiments for each blood sample analyzed. BC200 blood levels, shown as fold-increase in comparison with the control group (healthy subjects), at least doubled in patients with primary disease before surgery (group Primary Disease I) and in patients with metastatic disease (group Metastatic Disease). In the cases of group Primary Disease I, blood samples were collected before tumor resection. Subsequent to surgery (group Primary Disease II), levels of BC200 RNA in peripheral blood were reduced, indicating that BC200 blood levels correlate with tumor load. Statistical analysis: non-parametric Kruskal-Wallis analysis (P=0.005) followed by non-parametric Mann-Whitney U-test; P=0.003, *P=0.001. In this and the following figures, $2$-$\Delta\Delta Ct$ was calculated to represent the fold-increase of BC200 levels in a patient's blood sample, relative to control blood samples from healthy subjects (see Materials and Methods)[15]. (C) BC200 blood levels in former breast cancer patients with no evidence of current residual disease were indistinguishable from BC200 levels in healthy control subjects. qRT-PCR analysis shows that long-term disease-free former breast cancer patients exhibit baseline BC200 blood levels that are similar to those in healthy subjects. Statistical analysis: non-parametric Kruskal-Wallis analysis (P=0.668) followed by non-parametric Mann-Whitney U-test; P=0.674.

DETAILED DESCRIPTION OF THE INVENTION

Regulatory BC200 RNA is highly expressed in human mammary carcinoma cells. In the present invention, we demonstrate that BC200 RNA is detectable in peripheral blood of invasive breast cancer (IBC) patients. This discovery provides the means to quantify and characterize circulating BC200 circulating tumor cells, thereby providing a more sensitive test to monitor a patients progress and/or response to treatments.

Using quantitative reverse-transcriptase polymerase-chain-reaction (qRT-PCR) methodology we observed that BC200 blood levels were significantly elevated in IBC patients prior to tumorectomy and in metastatic breast cancer patients in comparison with healthy subjects (P=0.001 and P=0.003 respectively). In IBC patients who had undergone tumorectomy, BC200 blood levels were not distinguishable from levels in healthy subjects. In blood from IBC patients, BC200 RNA was specifically detected in the mononuclear leukocyte fraction. The qRT-PCR approach is sensitive enough to detect as few as three BC200-expressing tumor cells.

Thus, we have established the potential of BC200 blood levels to serve as a molecular indicator of invasive breast malignancy.

Diagnostic Assays for Breast Cancer Based on BC200 RNA Detection in Whole Blood

As described herein, detection of BC200 RNA in blood can be valuable in breast cancer diagnostic and prognostic methods. BC200 RNA detection can be employed on any type of biological sample where invasive breast cancers may be found, including but not limited to body fluids (including blood, serum, nipple aspirates), any type of cell (breast cancer tissue cells, circulating tumor cells in blood etc.) or body tissue.

In most embodiments for screening for the presence of BC200 RNA in blood, the BC200RNA nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art. Thus, BC200RNA levels can be directly determined without the need for to amplify the BC200 RNA target.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of RNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

In a preferred embodiment, blood is isolated from the patient and circulating BC200RNA levels determined relative to predetermined healthy control levels obtained from subjects without breast cancer. In an alternative embodiment, a mononuclear cell prep is prepared using Ficoll gradient separation for example. The peripheral blood mononuclear cells so isolated will contain any circulating breast cancer cells, if present in the whole blood sample. Nucleic acids are isolated from cells present in the preparation and subjected BC200RNA expression analysis.

Detection of such cells in circulation can provide the clinician with valuable information when considering treatment options for the patient.

In certain embodiments, the assay method can include determining the marker status of other markers associated with more aggressive breasts cancer including Her-2 neu, ErB, lymph node involvement and the like.

KITS AND ARTICLES OF MANUFACTURE

In another aspect of the invention, a kit is provided to facilitate the isolation and characterization of BC200 RNA expressing circulating tumor cells. Such a kit which may contain primers or probes suitable for BC200 RNA detection, reagents suitable for conducting PCR, reagents useful for performance of RLS or PWG, reagents useful for the isolation of PBMCs from whole blood, instructions for use, vials for conducting the reactions, an assay substrate, detectable labels or any combination thereof.

The following example is provided to illustrate certain embodiments of the invention. It is not intended to limit the invention in any way.

The following materials and methods are provided to facilitate the practice of the present invention.

Patient Recruitment and Inclusion/Exclusion Criteria

Peripheral blood was collected from the following groups:
(i) Healthy subjects: This group comprised apparently healthy women having no signs or symptoms of cancer (n=12).
(ii) No evidence of disease: This group comprised previous breast cancer patients who had completed treatment, including adjuvant therapy, at least 1.5 years prior to blood collection. These patients were under surveillance, with no evidence of current disease, at the time of blood collection (n=10).
(iii) Primary disease I: This group comprised patients with operable breast cancer after diagnosis but before resection of the primary tumor (n=14).
(iv) Primary disease II: This group comprised patients with operable breast cancer after tumorectomy, at the time of blood collection either undergoing adjuvant therapy or having recently completed adjuvant therapy, typically within one month before blood collection (n=12).
(v) Metastatic disease: This group comprised patients with active metastatic disease, stage IV (n=23).

Patient parameters are listed in Table 1. Patients' anamneses and oncological assessments were reviewed by two oncologists (R. L., G. A. S.).

Specimen Characteristics

Blood was obtained from the median cubital vein on the anterior forearm and collected in BD Vacutainer tubes containing EDTA (BD, Franklin Lakes, N.J., USA). 250 µl aliquots were quick-frozen at −80° C. A 250-µl aliquot typically generated 1.5 µg total RNA. 10 ng total RNA was used per reaction, i.e. 30 ng for triplicate BC200 amplification and 30 ng for triplicate control RNA amplification reaction, in total 60 ng per experiment. The study protocol was approved by the local Institutional Review Board, and written informed consent was obtained from each study participant.

RNA Isolation and qRT-PCR

Total RNA was extracted from 250 µl whole blood samples using the Ribopure Extraction Kit (Ambion, Austin, Tex., USA). RNA samples were treated with Turbo DNAfree (Ambion, USA) to minimize DNA contamination. After DNase treatment, each sample was tested for residual genomic DNA with an "RNA only" qRT-PCR reaction. Only samples that did not exhibit detectable DNA background signal were used in this work. The reverse transcriptase step was performed as follows, using random hexamer primers and SuperScript III (Invitrogen, Carlsbad, Calif., USA): 5 min at 25° C., 1 h at 50° C., 15 min at 70° C. PCR amplification reactions were carried out in a finale volume of 50 µl using 1.0 units of Platinum Taq DNA Polymerase (Invitrogen, Carlsbad, Calif., USA). PCR amplification conditions were as follows: 1 cycle of 1 min at 94° C., 45 s at 57° C., 1 min at 72° C., followed by 37 cycles of 30 s at 94° C., 45 s at 57° C., 1 min at 72° C., and a final cycle of 1 min at 94° C., 45 s at 57° C., 15 min 72° C. qRT-PCR was performed with the SYBR Green detection dye kit (Qiagen, Valencia, Calif., USA), using the ABI Prism-7000 Sequence Detection System (Applied Biosystems, Foster City, Calif., USA). Primers for the amplification of BC200 RNA were designed as follows:

BC200 Forward Primer: 5' CCTGGGCAATATAGCGAGAC 3'; SEQ ID NO: 1
BC200 Reverse Primer: 5' GGGTTGTTGCTTTGAGGGA 3'; SEQ ID NO: 2

The predicted amplification product corresponds to nt 91-188 of the 3' region of BC200 RNA. The 97-nt length PCR product was sequenced and verified as corresponding to the above 3' BC200 RNA segment. As an internal standard for qRT-PCR, we used the mRNA encoding acidic ribosomal protein (ARP, also known as ribosomal protein P0, NM_001002) [13]. ARP primers were used as described [13]. ARP mRNA was used to normalize the amount of total RNA in each qRT-PCR reaction [14]. As an independent internal control, we used primers specific for GAPDH (SABioscience, Frederick, Md., USA), as described by the manufacturer. qRT-PCR data were analyzed using the cycle threshold (Ct) method [15]. For each sample, the Ct for BC200 RNA was normalized to the Ct for ARP mRNA, resulting in a $\Delta$Ct that reflects the relative level of BC200 RNA in that sample. For a blood sample from a breast cancer patient, the $\Delta$Ct was normalized to the mean $\Delta$Ct obtained with samples from healthy subjects, resulting in a $\Delta\Delta$Ct for the patient sample. 2-$\Delta\Delta$Ct was then calculated as a measure of the fold-increase of BC200 RNA in the patient's blood sample, relative to control blood samples from healthy subjects.

Blood Fractionation

To prepare blood fractions (in particular the MNL fraction which includes circulating tumor cells, CTCs), we performed cell fractionation using the Ficoll-Paque procedure (Histopaque 1077, Sigma-Aldrich, St. Louis, Mo., USA), as described [16]. In brief, blood samples were diluted with PBS (without Ca2+ or Mg2+) and were layered on 3 ml of a Ficoll gradient. After centrifugation at 300 g for 10 minutes, MNL, RBC/PML (red blood cells/polymorphonuclear leukocytes), and plasma fractions were collected, washed with PBS, and RNA-extracted using Ribopure.

Limiting Dilution Experiments with MCF7 Cells

MCF7 cells (a human breast adenocarcinoma cell line; ATCC, Manassas, Va., USA) were used as a breast cancer cell system. For limiting dilution experiments, we used cell lysates to avoid random variations in the number of cells included in the assay.

Lysates of known numbers of MCF7 cells were prepared using lysis buffer (10 mM glycine, 1% Triton X-100). A given amount of MCF7 cell lysate, representing the desired number of cells, was then added to total RNA isolated from $10^4$ Baby Hamster Kidney (BHK) cells, or to 10 ng of total RNA isolated from blood of healthy subjects. BHK cells were obtained from ATCC (Manassas, Va., USA). Total RNA was prepared using TRIzol (Invitrogen, Carlsbad, Calif., USA). Samples were DNase-digested and reverse transcribed as described above.

Statistical Methods

Statistical analysis was performed on 71 blood samples in 5 groups. To analyze the significance of BC200 blood levels among groups, we used non-parametric Kruskal-Wallis one-way analysis of variance by ranks. The non-parametric Mann-Whitney U-test was used for comparisons of two groups. ROC analysis was used to establish discriminative power of BC200 RNA as a diagnostic and prognostic indicator. In ROC analysis, sensitivity is plotted against (1—specificity) [17]. The Area Under the Curve (AUC) is an index of the discriminative diagnostic power of a given test, with an ideally performing test having an AUC of 1.0. Statistical analysis was performed using SPSS software (Chicago, Ill., USA).

The following examples are provided to illustrate certain embodiments of the invention. They are not intended to limit the invention in any way.

Example I

BC200 RNA in Blood of Breast Cancer Patients

Figure 1:
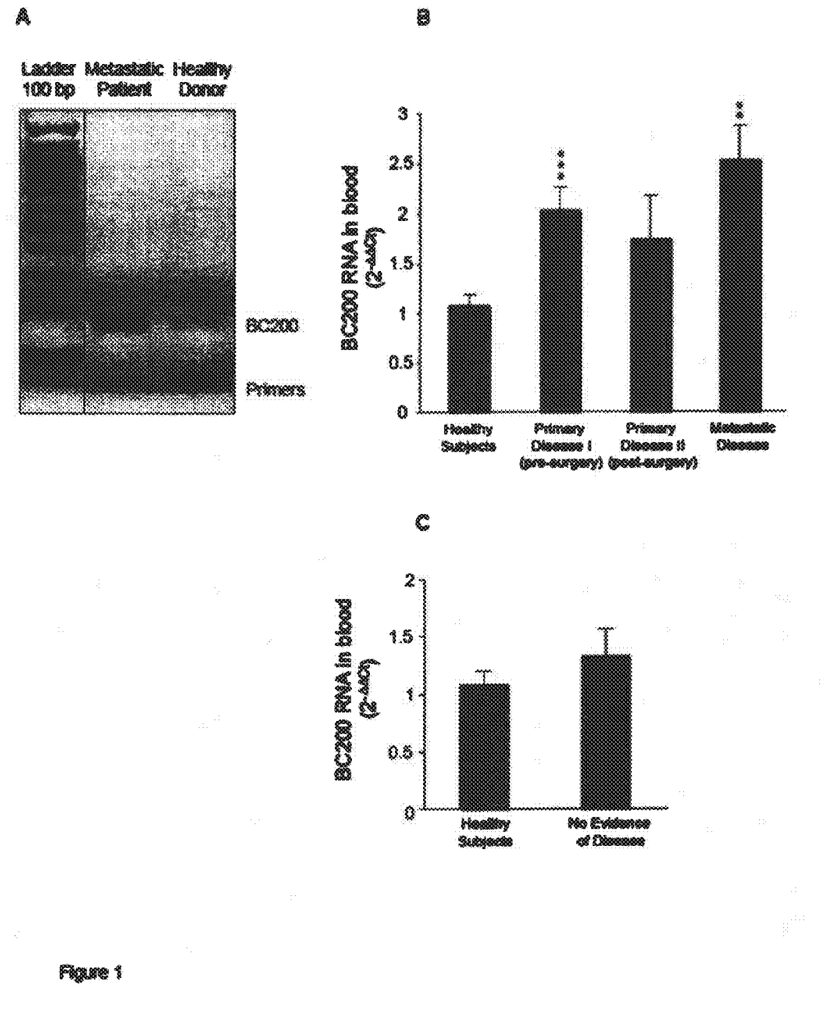

To establish whether BC200 RNA is detectable in peripheral blood of invasive breast cancer patients, we initially used RT-PCR methodology applied to blood from control subjects and breast cancer patients. RT-PCR amplification revealed that BC200 levels in blood from a breast cancer patient with metastatic disease were substantially higher than those from a healthy control subject (FIG. 1A).

We collected peripheral blood from a total of 71 subjects (Table 1). BC200 levels were established in blood samples from these subjects by qRT-PCR (also known as real-time RT-PCR). The results are shown in diagrammatic form in FIGS. 1B and C. High levels of BC200 RNA were detected in blood samples from breast cancer patients with active disease. BC200 blood levels were significantly elevated in patients with either primary or metastatic disease, in comparison with healthy subjects (FIG. 1B). Specifically, breast cancer patients with primary disease who had not yet undergone tumorectomy exhibited a substantial increase of BC200 levels (twofold in comparison to control group healthy subjects; FIG. 1B, group Primary Disease I). This increase was highly significant (*P=0.001, Mann-Whitney U-test), suggesting high discriminating power. Patients with metastatic disease (FIG. 1B, group Metastatic Disease) exhibited an almost two and half fold average increase of BC200 blood levels, in comparison to control group healthy subjects (P=0.003, Mann-Whitney U test). In post-surgery patients (FIG. 1B, group Primary Disease II), BC200 blood levels had decreased and were not significantly different from BC200 blood levels in healthy subjects. This result is consistent with the notion that BC200 RNA in peripheral blood of invasive breast cancer patients (i.e. group Primary Disease I) is contributed by circulating tumor cells (CTCs) that have been released from the primary tumor, and that further release of cells would cease after tumor resection. Similar observations have been reported after excision of primary malignancies other than breast cancer [18]. It is interesting to note, however, that the SEM in group Primary Disease II is relatively high, an indication of heterogeneity in BC200 blood levels in this patient group. It is possible that such heterogeneity correlates with varying treatment success, i.e. high BC200 levels indicating a relatively high number of residual CTCs.

Figure 2:
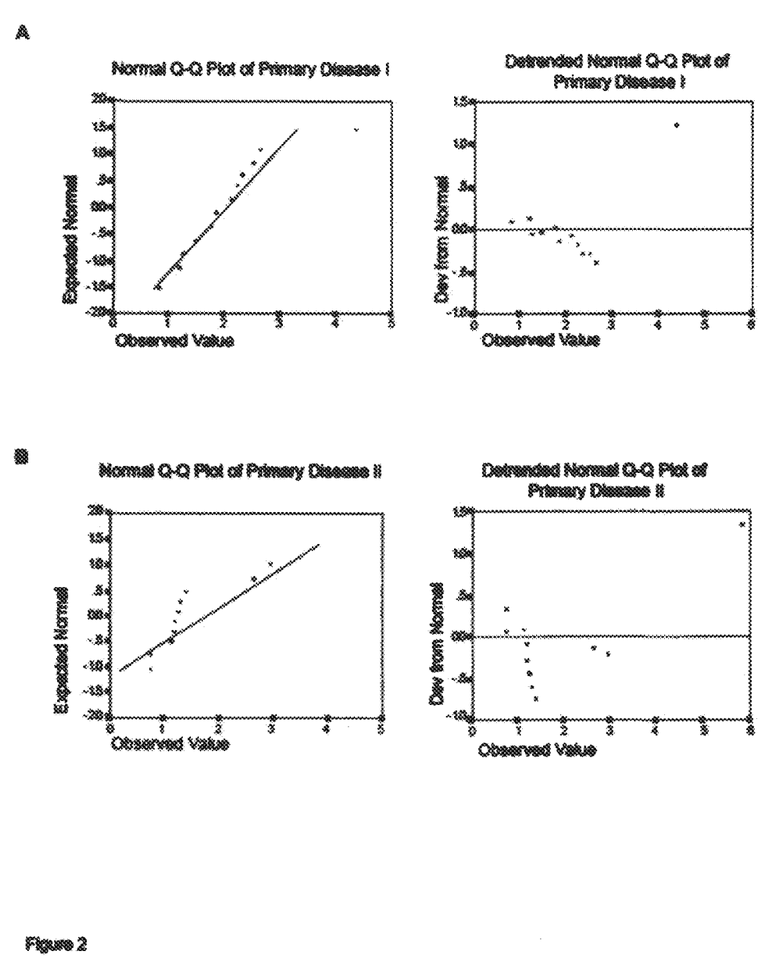
FIG. 2. Sample distribution analysis of Primary Disease I and Primary Disease II groups (normal and detrended normal Q-Q plots). Normality analysis of Primary Disease I (primary disease patients prior to tumorectomy) sample distribution shows no significant deviation from normal distribution (in green, A). Conversely, the Primary Disease II group (post-surgery primary disease patients) shows a statistical significant departure from normality (in green, B) with a Kolmogorov-Smirnov P<0.0005.

These observations were confirmed by normality analysis. Thus, normal Q-Q plots and detrended normal Q-Q plots for BC200 levels show that the distribution of the Primary Disease I group (FIG. 2A) conforms to a normal distribution (shown in green). Conversely, the group of post-surgery primary disease breast cancer patients indicated a marked departure from normal distribution (FIG. 2B), and Kolmogorov-Smirnov analysis of normality indicates high significance of this deviation (P<0.0005), which is consistent with a multiple population distribution. The skewness for this patient group was 2.3, a likely reflection of the presence within this group of individuals with high residual BC200 blood levels. See Table I.

Table I

| | Post-treatment Surveillance | Primary Disease I (pre-surgery) | Primary Disease II (post-surgery) | Metastatic Disease |
|---|---|---|---|---|
| Number of patients | 10 | 14 | 12 | 23 |
| Age (mean) | 62.9 | 59.1 | 53.8 | 53.7 |
| Pre-menopausal | 1 | 5 | 5 | 8 |
| Post-menopausal | 9 | 9 | 7 | 15 |
| Stage I | 6 | 0 | 1 | 0 |
| Stage II | 3 | 5 | 7 | 0 |
| Stage III | 1 | 9 | 4 | 0 |
| Stage IV | 0 | 0 | 0 | 23 |
| Tumor size 1-1.9 cm | 6 | 0 | 2 | 1 |
| Tumor size 2-3.9 cm | 1 | 3 | 7 | 2 |
| Tumor size > 4 cm | 1 | 11 | 3 | 14 |
| Unknown | 2 | 0 | 0 | 6 |
| Grade 1 or 2 | 3 | 5 | 3 | 6 |
| Grade 3 | 4 | 8 | 7 | 12 |
| Unknown | 3 | 1 | 2 | 5 |
| Lymph Node 0 | 7 | 3 | 6 | 4 |
| Lymph Node 1-3 | 3 | 11 | 6 | 15 |
| Unknown | 0 | 0 | 0 | 4 |
| Estrogen Receptor + | 6 | 7 | 8 | 15 |
| Estrogen Receptor − | 1 | 7 | 4 | 8 |
| Unknown | 3 | 0 | 0 | 0 |
| Progesterone Receptor + | 5 | 7 | 8 | 10 |
| Progesterone Receptor − | 2 | 7 | 4 | 13 |
| Unknown | 3 | 0 | 0 | 0 |
| Her2/neu + | 4 | 12 | 8 | 19 |
| Her2/neu − | 2 | 1 | 4 | 4 |
| Unknown | 4 | 1 | 0 | 0 |

We note that some intra-group heterogeneity was observed for BC200 blood levels in all patients groups, but for groups other than post-surgery primary disease patients, such deviation from normality did not reach statistical significance (Kolmogorov-Smirnov, P>0.2).

We also examined blood samples from former breast cancer patients with no evidence of residual disease. These patients had been undergoing surveillance for several years post-treatment and were considered disease-free at the time of blood sample collection. Notably, in blood samples from these patients, BC200 levels were significantly lower than in patients with active disease, primary or metastatic, and were in fact not significantly different from BC200 blood levels in healthy subjects (FIG. 1C).

Discriminative Diagnostic Power

Figure 3:
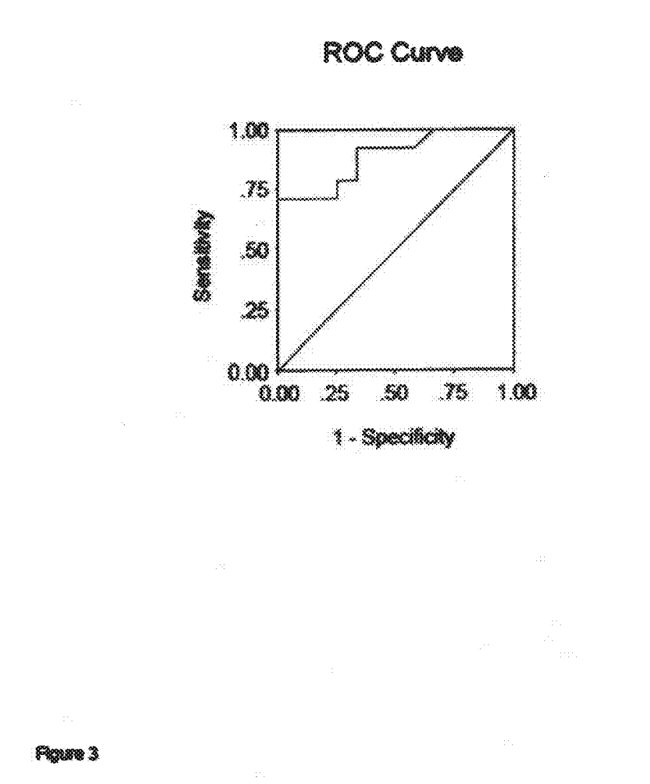
FIG. 3. ROC analysis of BC200 expression in peripheral blood of invasive breast cancer patients. To ascertain the discriminative diagnostic power of the BC200 blood test, ROC analysis was performed by plotting sensitivity against (1—specificity), comparing BC200 levels in blood from healthy subjects with BC200 levels in presurgery invasive breast cancer patients (group Primary Disease I). The obtained ROC Curve shows an AUC of 0.89 (95% confidence interval of 0.77-1.0), indicating a high discriminative efficacy of the BC200 test.

What is the discriminative power of the BC200 blood test? Receiver Operating Characteristic (ROC) analysis was performed to calculate the diagnostic efficacy of BC200 blood levels as a molecular indicator of invasive breast cancer, i.e. the ability of the test to correctly classify subjects with and without disease. In ROC analysis, sensitivity is plotted against (1—specificity), and the Area Under the Curve (AUC) is used as an index of diagnostic power, varying from 0.5 (no diagnostic power) to 1.0 (perfect diagnostic power) [17]. Comparing the pre-surgery invasive breast cancer group (Primary Disease I) with the healthy subjects group, an AUC of 0.89 (with a 95% confidence interval of 0.77-1.0) was obtained for BC200 blood levels (FIG. 3). These data indicate high discriminative power of BC200 RNA in peripheral blood as a molecular indicator of invasive breast cancer. They are in agreement with the observed lack of false positives in the healthy subject group (i.e. BC200 levels in all cases below mean±SEM of Primary Disease I group). Analogously, an AUC of 0.81 (95% confidence interval: 0.67-0.95) was obtained when comparing the metastatic disease group with the healthy subjects group, again indicating high discriminating diagnostic power (not shown).

BC200 Levels in Cellular Fractions from Peripheral Blood

The data obtained are consistent with the notion that cancer cells expressing BC200 RNA enter the circulation as CTCs. If so, BC200 RNA would be expected to become detectable in the white blood cell fraction (i.e. mononuclear leukocytes). To test this hypothesis, we performed Ficoll fractionation of blood from invasive breast cancer patients. We separated three blood fractions: plasma, mononuclear leukocytes (MNL, also called buffy coat), and red blood cells (RBC), a fraction containing also polymorphonuclear leukocytes (PML).

BC200 levels in MNL fractions from breast cancer patients were increased by more than twofold, in comparison with MNL fractions from healthy donors (Table 2). In PML/RBC fractions (containing mainly anucleate erythrocytes), BC200 RNA could not be reliably detected in samples from either breast cancer patients or healthy subjects (Table 2). BC200 RNA was also not detectable in plasma fractions from breast cancer patients, a result to suggest that BC200 RNA is not released into the circulation in acellular form, i.e. as "free RNA". The BC200 approach can thus reliably detect BC200 RNA in the MNL fraction from peripheral blood of invasive breast cancer patients. The data also suggest that BC200 levels in peripheral blood are in fact reflecting the presence of CTCs that express the RNA.

TABLE 2

| Blood fraction | BC200 Level $2^{-\Delta\Delta Ct} \pm$ SEM | Student's t test |
|---|---|---|
| MNL | 2.24 + 0.56 | P < 0.05 |
| PML + RBC | Nd | — |
| Plasma | Nd | — |

Table 2. Expression of BC200 RNA in the mononuclear cell fraction of peripheral blood of breast cancer patients. Total RNA was isolated after cell fractionation, and qRT-PCR was performed with three fractions: mononuclear leukocytes (MNL containing CTCs), polymorphonuclear leukocytes and red blood cells (PML and RBC) and plasma. BC200 levels were elevated in the MNL cell fraction from breast cancer patients, compared with the MNL cell fractionation from the control healthy subjects group. In PML/RBC fractions, BC200 RNA was not reliably detectable (ND) by qRT-PCR. BC200 RNA was also not detected in plasma. $2^{-\Delta\Delta Ct}$ represents the fold-increase of BC200 levels in a patient's blood sample, relative to blood samples from healthy subjects.

Sensitivity of BC200 RNA in Cancer Cell Detection

Figure 4:
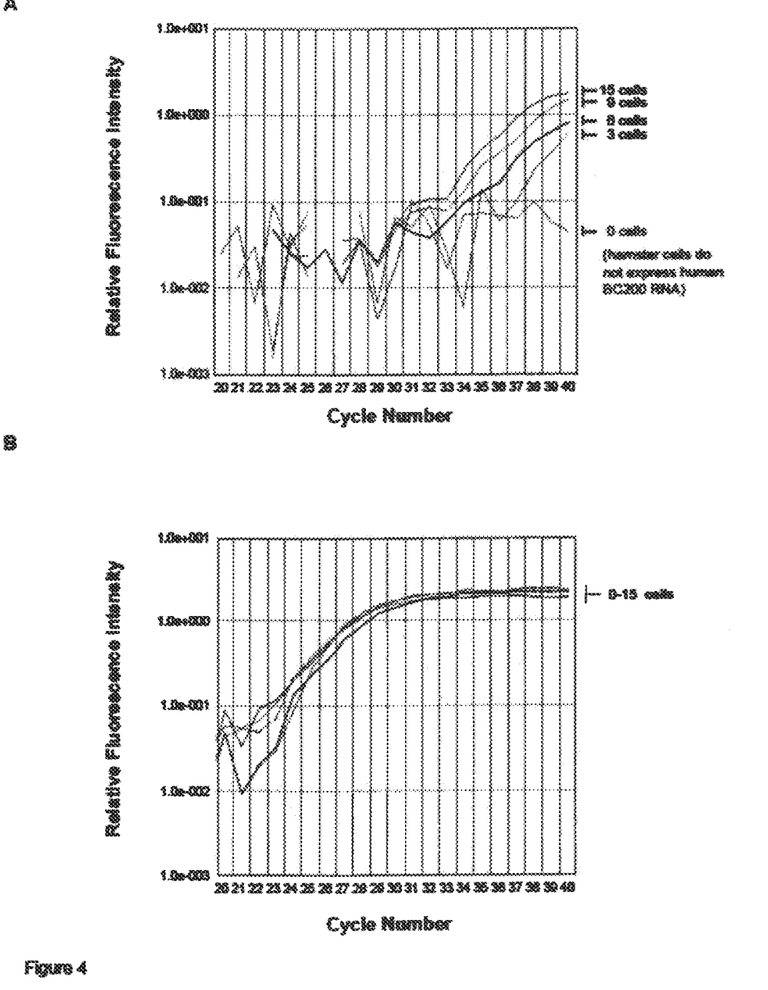
FIG. 4. Limiting dilution experiments: MCF7 breast cancer cell RNA in BHK cell RNA. (A) The panel shows qRT-PCR amplification plots for BC200 RNA. Total RNA isolated from MCF7 cells, representing the respective number of cells indicated, was diluted with total RNA from 104 BHK cells and subjected to qRT-PCR amplification. The curves show that BC200 amplification allowed detection of as few as three MCF7 cells. The zero MCF7 cells sample failed to reach amplification threshold after 40 cycles, indicating that no BC200 RNA was detected. (B) Control amplification experiments were performed with ARP mRNA. In contrast to BC200 amplification, ARP amplification resulted in plots that were grouped together, indicating constant expression independent of MCF7 cell numbers.

How sensitive is the BC200 approach, i.e. what is the minimum number of cancer cells that it can reliably detect? To address this question, we performed limiting dilution experiments using MCF7 breast cancer cells. Total RNA from given numbers of MCF7 cells was analyzed against a background of total RNA from $10^4$ cultured BHK cells. (Non-primate BHK cells do not express human BC200 RNA.) The qRT-PCR amplification plot (FIG. 4) show that the BC200 test can detect as few as three MCF7 cells, and that it can detect small changes in the number of such cells (FIG. 4). BC200 RNA is thus a highly sensitive indicator of epithelial breast cancer cells in blood. Conversely, the mRNA encoding the housekeeping protein ARP produced amplification plots that clustered together (FIG. 4), i.e. not reflecting the number of MCF7 cells used. This result was expected considering that the gene is constitutively expressed at relatively high levels irrespective of cell type.

Figure 5:
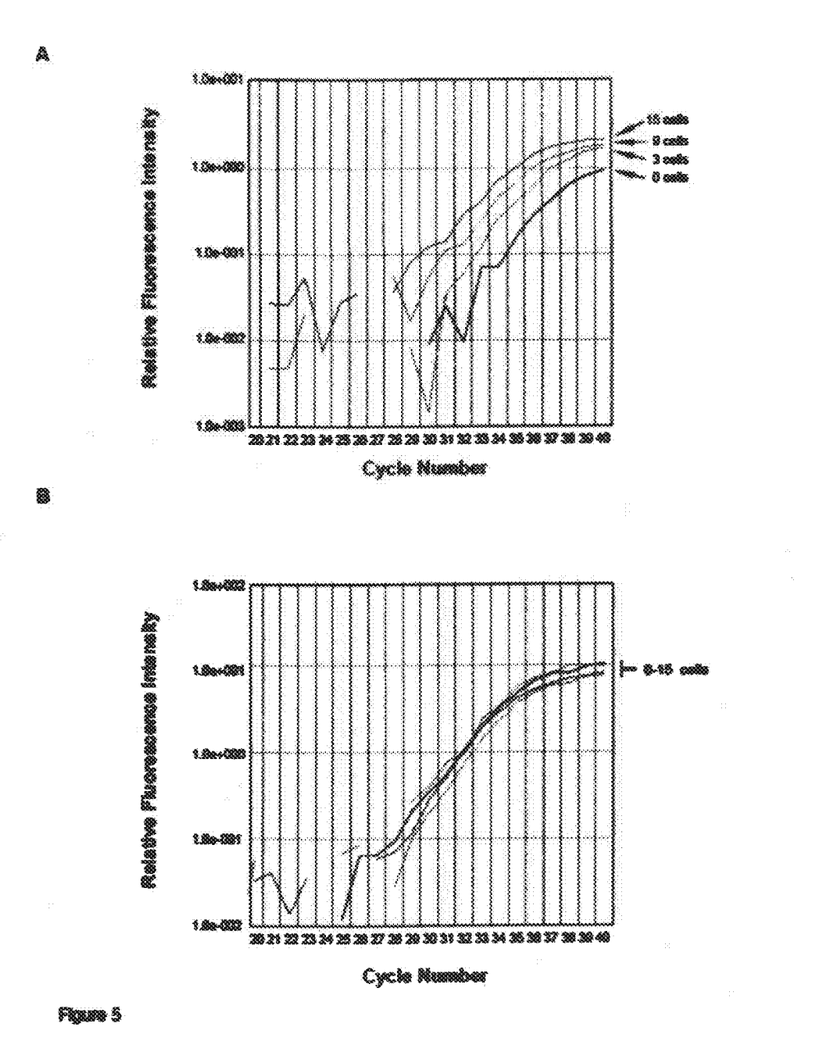
FIG. 5. Limiting dilution experiments: MCF7 breast cancer cell RNA in RNA from blood of healthy subjects. (A) The panel shows qRT-PCR amplification plots for BC200 RNA. Total RNA isolated from MCF7 cells (from 3 to 15 cells) was diluted with total RNA (10 ng) from blood of healthy subjects. BC200 qRT-PCR amplification allowed detection of three MCF7 cells. (B) Control amplification experiments were performed with GAPDH mRNA. As in the experiments with ARP mRNA, GAPDH amplification plots were grouped together.

Analogous limiting dilution experiments were performed in which RNA from MCF7 breast cancer cells was analyzed against a background of RNA from whole blood of healthy subjects. Using both ARP and GAPDH mRNAs as internal qRT-PCR standards, we were able to detect BC200 RNA from 3 MCF7 cells (FIG. 5). BC200 levels in samples containing 3 MCF7 cell equivalents were significantly elevated, compared with samples containing 0 MCF7 cell equivalents (Student's t-test, P=0.0325). The strength of the qRT-PCR BC200 signal again increased proportionally with the number of MCF7 cell equivalents (FIG. 5). MCF7 BC200 levels were established against the same amount of total RNA from blood of healthy subjects per amplification reaction that was used above in FIG. 1 (see also Materials and Methods).

The amplification signal in 0 MCF7 cell samples is consistent with the baseline expression of BC200 RNA in normal blood (see also FIGS. 1A and 1B). It should also be noted that expression of BC200 RNA in MCF7 cells is lower than expression of BC200 RNA in primary invasive mammary carcinoma cells (by a factor of 7; unpublished). The combined data indicate that detection of circulating primary breast cancer cells via BC200 expression should be even more sensitive than detection of MCF7 cells.

DISCUSSION

The significance of regulatory RNAs in eukaryotic cellular form and function is increasingly being recognized [1]. However, the role of such RNAs in tumorigenesis and tumor development, and their potential utility as clinical tools, remains poorly understood and under-explored. We have previously reported that human BC200 RNA is expressed at high levels in invasive breast cancer cells [7]. We now show that in patients with invasive breast cancer, BC200 RNA can be detected in peripheral blood with high specificity and sensitivity. These data will form the basis for future longitudinal studies aimed at the potential of BC200 RNA as a minimally invasive molecular indicator of breast malignancies.

We have developed qRT-PCR methodology that allows us to discriminate, with high consistency and reliability, BC200 blood levels in invasive breast cancer patients from those in healthy subjects and in past breast cancer patients with no evidence of recurrent disease. The difference between the untreated invasive disease subjects group and the healthy subjects group is statistically highly significant (P=0.001), and ROC analysis confirmed high specificity and sensitivity of the approach (AUC=0.89).

Mammography has a median sensitivity of 79 percent, ranging form 74 to 85 percent [19; 20]. We therefore propose that a BC200 blood test should be a valuable clinical complement to mammography in screening for breast cancer. Of all malignancies examined, only adenocarcinomas of the breast, mucoepidermoid carcinomas of the parotid, and melanomas were found to express high levels of BC200 RNA [6]. Thus, a screening result of elevated BC200 blood levels would be an indication of the presence of one of these malignancies (which can easily be differentiated). Although the difference between BC200 blood levels in untreated invasive breast cancer patients and healthy subjects is highly significant, some heterogeneity of BC200 levels was observed in the former (but not the latter) group. It is possible that in those cases within the untreated disease group that exhibited a smaller than average increase in BC200 blood levels, the number of cancer cells that have been released into the circulation was lower than group average. Lower BC200 levels in the peripheral blood of such patients may be a prognosticator of better outcome. The converse situation was encountered in breast cancer patients who have undergone treatment (i.e. resection and adjuvant therapy). Average BC200 blood levels in this group were not significantly different from levels in the healthy subjects group, indicating that treatment has resulted in a significant reduction of BC200-expressing cells. This result is consistent with previous observations that treatment can reduce tumor cell numbers in blood [18]. Nonetheless, some patients in this group exhibited elevated BC200 levels even after treatment. Accordingly, we hypothesize that treatment efficacy may have been suboptimal in such cases, with an analogously poorer prognosis for ultimate outcome. Such information may become valuable for individual breast cancer treatment decisions and outcome predictions. Prospective studies will be needed to examine whether high residual BC200 blood levels after treatment can serve as an index of high relapse potential.

No suitable molecular indicators are currently available for invasive breast cancer. Historically, tumor biomarker development has often been beset with difficulties [21]. Even PSA, widely used for prostate cancer screening, is of limited clinical utility due to its rather poor sensitivity and specificity [22]. We suggest that one underlying reason for the paucity of suitable molecular tumor markers is the limited stability and/or availability of traditionally used mRNAs or proteins. This contrasts with the high stability and abundance of a regulatory RNA such as BC200 RNA, molecular features that result in superior reliability and consistency of detection. Thus, our work demonstrates the clinical utility of BC200 RNA as a minimally invasive, highly discriminating molecular indicator of invasive breast malignancies.

Example II

Detection of BC200 RNA in the Clinical Setting

The information herein above can be applied clinically to patients for diagnosing an increased susceptibility for developing invasive breast cancer and therapeutic intervention. A preferred embodiment of the invention comprises clinical application of the information described herein to a patient. Diagnostic compositions, including microarrays, and methods can be designed to identify and quantify circulating BC200RNA from a patient to assess susceptibility for developing breast cancer, particularly aggressive invasive breast cancer. This can occur after a patient arrives in the clinic; the patient has blood drawn, and using the diagnostic methods described herein, a clinician can detect the levels of BC200RNA present in blood in order to monitor progress, recurrence or the efficacy of particular therapies. The information obtained from the patient sample, which can optionally be amplified prior to assessment, will be used to diagnose a patient with an increased or decreased susceptibility for developing invasive breast cancer. Kits for performing the diagnostic method of the invention are also provided herein. Such kits comprise a microarray comprising at least one BC200 RNA detection reagent and the necessary reagents for assessing the patient samples as described above.

The identity of elevated circulating BC200RNA levels will identify those that possess an altered risk for developing aggressive breast cancer. The information provided herein allows for therapeutic intervention at earlier times in disease progression that previously possible. Also, BC200 RNA provides a novel target for the development of new therapeutic agents efficacious for the treatment of breast cancer.

REFERENCES

[1] J. Barciszewski, and V. A. Erdmann, (Eds.) (2003) Noncoding RNAs: molecular biology and molecular medicine, Landes Bioscience, Georgetown.

[2] J. S. Mattick, Challenging the dogma: the hidden layer of non-protein-coding RNAs in complex organisms. BioEssays 25 (2003) 930-939.

[3] H. Wang, A. Iacoangeli, S. Popp, I. A. Muslimov, H. Imataka, N. Sonenberg, I. B. Lomakin, and H. Tiedge, Dendritic BC1 RNA: functional role in regulation of translation initiation. J. Neurosci. 22 (2002) 10232-10241.

[4] H. Wang, A. Iacoangeli, D. Lin, K. Williams, R. B. Denman, C. U. T. Hellen, and H. Tiedge, Dendritic BC1 RNA in translational control mechanisms. J Cell Biol 171 (2005) 811-21.

[5] D. Lin, T. V. Pestova, C. U. Hellen, and H. Tiedge, Translational control by a small RNA: dendritic BC1 RNA targets the eukaryotic initiation factor 4A helicase mechanism. Mol Cell Biol 28 (2008) 3008-19.

[6] W. Chen, W. Böcker, J. Brosius, and H. Tiedge, Expression of neural BC200 RNA in human tumours. J. Pathol. 183 (1997) 345-351.

[7] A. Iacoangeli, Y. Lin, E. J. Morley, I. A. Muslimov, R. Bianchi, J. Reilly, J. Weedon, R. Diallo, W. Böcker, and H. Tiedge, BC200 RNA in invasive and preinvasive breast cancer. Carcinogenesis 25 (2004) 2125-2133.

[8] A. Jemal, R. Siegel, E. Ward, Y. Hao, J. Xu, T. Murray, and M. J. Thun, Cancer statistics, 2008. CA Cancer J Clin 58 (2008) 71-96.

[9] P. T. Huynh, A. M. Jarolimek, and S. Daye, The false-negative mammogram. Radiographics 18 (1998) 1137-54.

[10] M. Kriege, C. T. Brekelmans, C. Boetes, P. E. Besnard, H. M. Zonderland, I. M. Obdeijn, R. A. Manoliu, T. Kok, H. Peterse, M. M. Tilanus-Linthorst, S. H. Muller, S. Meijer, J. C. Oosterwijk, L. V. Beex, R. A. Tollenaar, H. J. de Koning, E. J. Rutgers, and J. G. Klijn, Efficacy of MRI and mammography for breast-cancer screening in women with a familial or genetic predisposition. N Engl J Med 351 (2004) 427-37.

[11] M. Kriege, C. T. Brekelmans, I. M. Obdeijn, C. Boetes, H. M. Zonderland, S. H. Muller, T. Kok, R. A. Manoliu, A. P. Besnard, M. M. Tilanus-Linthorst, C. Seynaeve, C. C. Bartels, R. Kaas, S. Meijer, J. C. Oosterwijk, N. Hoogerbrugge, R. A. Tollenaar, E. J. Rutgers, H. J. de Koning, and J. G. Klijn, Factors affecting sensitivity and specificity of screening mammography and MRI in women with an inherited risk for breast cancer. Breast Cancer Res Treat 100 (2006) 109-19.

[12] H. Tiedge, W. Chen, and J. Brosius, Primary structure, neural-specific expression, and dendritic location of human BC200 RNA. J. Neurosci. 13 (1993) 2382-2390.

[13] J. Iqbal, K. Dai, T. Seimon, R. Jungreis, M. Oyadomari, G. Kuriakose, D. Ron, I. Tabas, and M. M. Hussain, IRE1β inhibits chylomicron production by selectively degrading MTP mRNA. Cell Metab 7 (2008) 445-55.

[14] I. Bieche, F. Lerebours, S. Tozlu, M. Espie, M. Marty, and R. Lidereau, Molecular profiling of inflammatory breast cancer: identification of a poor-prognosis gene expression signature. Clin Cancer Res 10 (2004) 6789-95.
[15] K. J. Livak, and T. D. Schmittgen, Analysis of relative gene expression data using real-time quantitative PCR and the 2-ΔΔCT Method. Methods 25 (2001) 402-8.
[16] M. Fraczek, D. Sanocka, M. Kamieniczna, and M. Kurpisz, Proinflammatory cytokines as an intermediate factor enhancing lipid sperm membrane peroxidation in in vitro conditions. J Androl 29 (2008) 85-92.
[17] J. A. Hanley, and B. J. McNeil, The meaning and use of the area under a receiver operating characteristics (ROC) curve. Radiology 143 (1982) 29-36.
[18] H. Patel, N. Le Marer, R. Q. Wharton, Z. A. Khan, R. Araia, C. Glover, M. M. Henry, and T. G. Allen-Mersh, Clearance of circulating tumor cells after excision of primary colorectal cancer. Ann. Surg. 235 (2002) 226-31.
[19] D. L. Miglioretti, R. Smith-Bindman, L. Abraham, R. J. Brenner, P. A. Carney, E. J. Bowles, D. S. Buist, and J. G. Elmore, Radiologist characteristics associated with interpretive performance of diagnostic mammography. J Natl Cancer Inst 99 (2007) 1854-63.
[20] S. Taplin, L. Abraham, W. E. Barlow, J. J. Fenton, E. A. Berns, P. A. Carney, G. R. Cutter, E. A. Sickles, D. Carl, and J. G. Elmore, Mammography facility characteristics associated with interpretive accuracy of screening mammography. J Natl Cancer Inst 100 (2008) 876-87.
[21] L. M. McShane, D. G. Altman, W. Sauerbrei, S. E. Taube, M. Gion, and G. M. Clark, Reporting recommendations for tumor marker prognostic studies (REMARK). J Natl Cancer Inst 97 (2005) 1180-4.
[22] M. B. Garnick, and W. R. Fair, Combating prostate cancer. Sci. Am. 279 (1998) 75-83.

While the invention has been described in detail and with reference to specific examples thereof, it will be apparent to one skilled in the art that various changes and modifications can be made therein without departing from the spirit and scope thereof.

What is claimed is:

1. A method for detecting circulating breast cancer cells comprising BC200 RNA, a molecular indicator of invasive breast malignancy in fractionated whole blood obtained from a patient, said method comprising:
   a) obtaining a whole blood sample from said patient;
   b) isolating a peripheral blood mononuclear cell (PBMC) fraction from said whole blood sample;
   c) extracting total RNA from said cells in step b);
   d) amplifying by polymerase chain reaction (PCR) BC200 RNA present in said total RNA, with a Forward Primer consisting of SEQ ID NO: 1 and a reverse primer consisting of SEQ ID NO: 2, said BC200 RNA being obtained from circulating breast cancer cells present within said PBMC fraction; and
   e) determining the number of circulating breast cancer cells in said PBMC fraction in patients based on BC200 RNA expression levels identified in step d), said method having sensitivity to detect as few as three circulating breast cancer cells in said PBMC fraction when present.

2. A kit for practicing the method of claim 1, comprising reagents necessary for the isolation and quantification of circulating breast cancer cells having BC200 RNA and instructional materials, a Ficoll gradient media, reagents for performing PCR, a sample from a control patient without evidence of disease, a detectably labeled oligonucleotide primer consisting of SEQ ID NO: 1, and a detectably labeled oligonucleotide primer consisting of SEQ ID NO: 2 and optionally a microarray.

3. The method of claim 1, further comprising identifying additional breast cancer markers present on said isolated cells.

4. The method of claim 1, further comprising identifying the levels of BC200 RNA present in the lymph nodes of said patient.

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: BC200 Forward Primer

<400> SEQUENCE: 1
cctgggcaat atagcgagac                                           20

<210> SEQ ID NO 2
<211> LENGTH: 19
<212> TYPE: DNA
<213> ORGANISM: Artificial Sequence
<220> FEATURE:
<223> OTHER INFORMATION: BC200 Reverse Primer

<400> SEQUENCE: 2
gggttgttgc tttgaggga                                            19

5. The method of claim 1, wherein BC200 mRNA levels are 2-2.5 fold higher than levels observed in patients without evidence of disease.

\* \* \* \* \*